(12) United States Patent
Nomoto et al.

(10) Patent No.: US 8,771,247 B2
(45) Date of Patent: *Jul. 8, 2014

(54) ABSORBENT ARTICLE WITH SIDE GATHERS

(75) Inventors: Takashi Nomoto, Kanonji (JP); Masashi Uda, Kanonji (JP); Hideaki Morita, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 530 days.

This patent is subject to a terminal disclaimer.

(21) Appl. No.: 12/666,550

(22) PCT Filed: Jun. 23, 2008

(86) PCT No.: PCT/JP2008/061403
§ 371 (c)(1),
(2), (4) Date: Feb. 23, 2010

(87) PCT Pub. No.: WO2009/004941
PCT Pub. Date: Jan. 8, 2009

(65) Prior Publication Data
US 2010/0174261 A1 Jul. 8, 2010

(30) Foreign Application Priority Data
Jun. 29, 2007 (JP) ................................ 2007-172429

(51) Int. Cl.
*A61F 13/15* (2006.01)
*A61F 13/20* (2006.01)

(52) U.S. Cl.
USPC .......... 604/385.101; 604/385.01; 604/385.04; 604/385.28

(58) Field of Classification Search
USPC ........................... 604/385.04, 385.28, 385.01
See application file for complete search history.

(56) References Cited

U.S. PATENT DOCUMENTS

| | | |
|---|---|---|
| 5,704,928 A | 1/1998 | Morita et al. |
| 2001/0020157 A1* | 9/2001 | Mizutani et al. ......... 604/385.04 |

(Continued)

FOREIGN PATENT DOCUMENTS

| | | |
|---|---|---|
| EP | 1 132 069 | 9/2001 |
| JP | 4-42817 | 4/1992 |

(Continued)

OTHER PUBLICATIONS

Extended European search report mailed Feb. 1, 2012, directed to European Application No. 08777514.4; 4 pages.

(Continued)

*Primary Examiner* — Melanie Hand
*Assistant Examiner* — Aundria Hairell
(74) *Attorney, Agent, or Firm* — Morrison & Foerster LLP

(57) ABSTRACT

An absorbent article that is favorable in the erection stability of gathers and excels in transversal leakage preventing effects. A pair of gathers of an absorbent article has a three-dimensional configuration part. The three-dimensional configuration part is formed so as to construct a hollow. A first junction edge portion is formed on the inward side in the width direction of the absorbent article and a second junction edge portion is provided on the outward side in the width direction of the absorbent article. The first junction edge portion is located on the area of the surface layer on which the absorbent body is disposed. The second junction edge portion, in at least the area where the pair of wings are disposed, is located on the area of the surface layer and/or backside layer more outward in the width direction than the periphery of the absorbent body.

9 Claims, 6 Drawing Sheets

(56) References Cited

U.S. PATENT DOCUMENTS

| | | |
|---|---|---|
| 2003/0028167 A1 | 2/2003 | Kashiwagi et al. |
| 2003/0120246 A1 | 6/2003 | Franklin et al. |
| 2007/0073259 A1* | 3/2007 | Erdman et al. ............ 604/385.28 |
| 2010/0191209 A1 | 7/2010 | Nomoto et al. |

FOREIGN PATENT DOCUMENTS

| | | |
|---|---|---|
| JP | 4-325153 | 11/1992 |
| JP | 8-503638 | 4/1996 |
| JP | 11-19123 | 1/1999 |
| JP | 11-299821 | 11/1999 |
| JP | 2000-288025 | 10/2000 |
| JP | 2000-325395 | 11/2000 |
| JP | 2003-24384 | 1/2003 |
| JP | 2003-210525 | 7/2003 |
| JP | 2003-245306 | 9/2003 |
| JP | 2006-115957 | 5/2006 |
| JP | 2006-311939 | 11/2006 |
| WO | WO-94/12135 | 6/1994 |

OTHER PUBLICATIONS

International Search Report mailed Aug. 19, 2008, directed at International Application No. PCT/JP2008/061403; 2 pages.
International Search Report mailed Aug. 19, 2008, directed to International Application No. PCT/JP2008/061403; 2 pages.
Nomoto et al., U.S. Office Action mailed Oct. 25, 2012, directed to U.S. Appl. No. 12/666,596; 15 pages.
Notice of Reasons for Rejection mailed Jan. 10, 2012, directed towards Japanese Application No. 2011-135410; 4 pages.
Notice of Reasons for Rejection mailed Aug. 16, 2011, directed towards Japanese Application No. 2011-135410; 2 pages.
Nomoto et al., U.S. Office Action mailed May 10, 2013, directed to U.S. Appl. No. 12/666,596; 17 pages.
Office Action mailed Nov. 18, 2013, directed to TW Application No. 097124264; 7 pages.
Nomoto et al., U.S. Office Action mailed Aug. 30, 2013, directed to U.S. Appl. No. 12/666,596; 23 pages.
Office Action mailed Jan. 3, 2014, directed to TW Application No. 097124263; 10 pages.

* cited by examiner

ABSORBENT ARTICLE WITH SIDE GATHERS

REFERENCE TO RELATED APPLICATION

This application is a national stage application under 35 USC 371 of International Application No. PCT/JP2008/061403, filed Jun. 23, 2008, which claims the priority of Japanese Application No. 2007-172429, filed Jun. 29, 2007, the contents of which prior applications are incorporated herein by reference.

FIELD OF THE INVENTION

The present invention relates to an absorbent article such as sanitary napkins, panty liners, disposable diaper and the like.

BACKGROUND OF THE INVENTION

Conventionally known as an absorbent article such as a sanitary napkin is an elongated absorbent article which includes a liquid-permeable surface layer, a liquid-impermeable back layer, a liquid-retainable absorbent layer arranged between the surface layer and the back layer, and a pair of wings on both sides in the longitudinal direction. Such an absorbent article is usually used, at the time of wearing, in such a way that the pair of wings are folded back and fastened to an external surface of a crotch area such as undergarment.

Moreover, it is also known to form three-dimensional gathers which stand up on the wearer's skin side in both sides of the absorbent article in order to improve the leakproof property in both sides in the longitudinal direction in the absorbent article.

As an absorbent article including a pair of wings and a pair of three-dimensional gathers, Japanese Unexamined Patent Application Publication No. 2003-210525 discloses an absorbent article including a pair of wings which are provided with, as the origin, external surfaces of the standing three-dimensional gathers and portions between the base and the top of the three-dimensional gathers.

SUMMARY OF THE INVENTION

Problems to be Solved by the Invention

The absorbent article as described in Japanese Unexamined Patent Application Publication No. 2003-210525 prevents the three-dimensional wings, which are provided adjacently to the wings, from collapsing inward due to the outward tension in the width direction occurring at the time of folding back the pair of wings.

However, in the absorbent article as described in Japanese Unexamined Patent Application Publication No. 2003-210525, the three-dimensional gathers collapse outward by contraries, depending on the tension to the wings at the time of folding back the wings, as a result of which the absorbent article is worn in a state where the three-dimensional gathers have collapsed outward, thereby leading to the side leakage.

Accordingly, an object of the present invention is to provide an absorbent article, which has a superior standing stability of the gathers, and which has a superior effect of preventing the side leakage.

Means for Solving the Problems

The present invention achieves the aforementioned object by an elongated absorbent article, which includes a surface layer; a back layer; an absorbent layer having arranged between these; a pair of gathers which are formed to be separated from each other in both sides of a longitudinal direction in the surface layer, and which are configured to have a hollow portion by a sheet member; and a pair of wings which are formed by extending the surface layer and/or the back layer outward in a width direction of the absorbent layer. Each of the pair of gathers is formed in such a way that the sheet member has a three-dimensional-shaped portion, and that the three-dimensional-shaped portion is joined to the surface layer and/or the back layer by a connecting portion which is formed to extend in the longitudinal direction of the absorbent article, the three-dimensional-shaped portion configuring the hollow portion. The connecting portion includes a first connecting end which forms an end inward in a width direction in the three-dimensional-shaped portion, and a second connecting end which forms an end outward in the width direction in the three-dimensional-shaped portion. The first connecting end is located in a region in which the absorbent body is arranged in the surface layer. The second connecting end is located in a region more outward in the width direction than an outer edge of the absorbent body in the surface layer and/or the back layer, at least in regions in which the pair of wings are arranged.

More specifically, the present invention provides the following.

In a first aspect of an absorbent article of the present invention, the elongated absorbent article includes a surface layer having an at least partly liquid-permeable surface sheet; a back layer having a liquid-impermeable back sheet; an absorbent layer having a liquid-retainable absorbent body arranged between these; a pair of gathers which are formed to be separated from each other in both sides of a longitudinal direction in the surface layer, and which are configured to have a hollow portion by a sheet member; and a pair of wings which are formed by extending the surface layer and/or the back layer outward in a width direction of the absorbent layer, in which each of the pair of gathers is formed in such a way that the sheet member has a three-dimensional-shaped portion which is convex on a skin contacting side of the absorbent article, and that the three-dimensional-shaped portion is joined to the surface layer and/or the back layer by a connecting portion which is formed to extend in the longitudinal direction of the absorbent article, the three-dimensional-shaped portion configuring the hollow portion, in which the connecting portion comprises a first connecting end which forms an end inward in a width direction in the three-dimensional-shaped portion, and a second connecting end which forms an end outward in the width direction in the three-dimensional-shaped portion, in which the first connecting end is located in a region in which the absorbent body is arranged in the surface layer, and in which the second connecting end is located in a region more outward in the width direction than an outer edge of the absorbent body in the surface layer and/or the back layer, at least in regions in which the pair of wings are arranged.

In a second aspect of the absorbent article as described in the first aspect of the present invention, the distance between the first and the second connecting ends in a vicinity of both ends in the longitudinal direction of the absorbent article is greater than the distance between the first and the second connecting ends in a central portion in the longitudinal direction of the absorbent article, and wherein the pair of wings are arranged in the central portion in the longitudinal direction.

In a third aspect of the absorbent article as described in any one of the first or second aspect of the present invention, at least a face on the surface-layer side of the pair of wings is formed with the sheet member.

In a fourth aspect of the absorbent article as described in any one of the first to third aspects of the present invention, each of the pair of gathers has a plurality of elastic members, in which the plurality of elastic members are arranged on a surface, or inside, the sheet member, and are arranged along the longitudinal direction.

Effects of the Invention

According to the present invention, it is possible to provide an absorbent article, which has a superior standing stability of the gathers, and which has a superior effect of preventing the side leakage.

Figure 1:
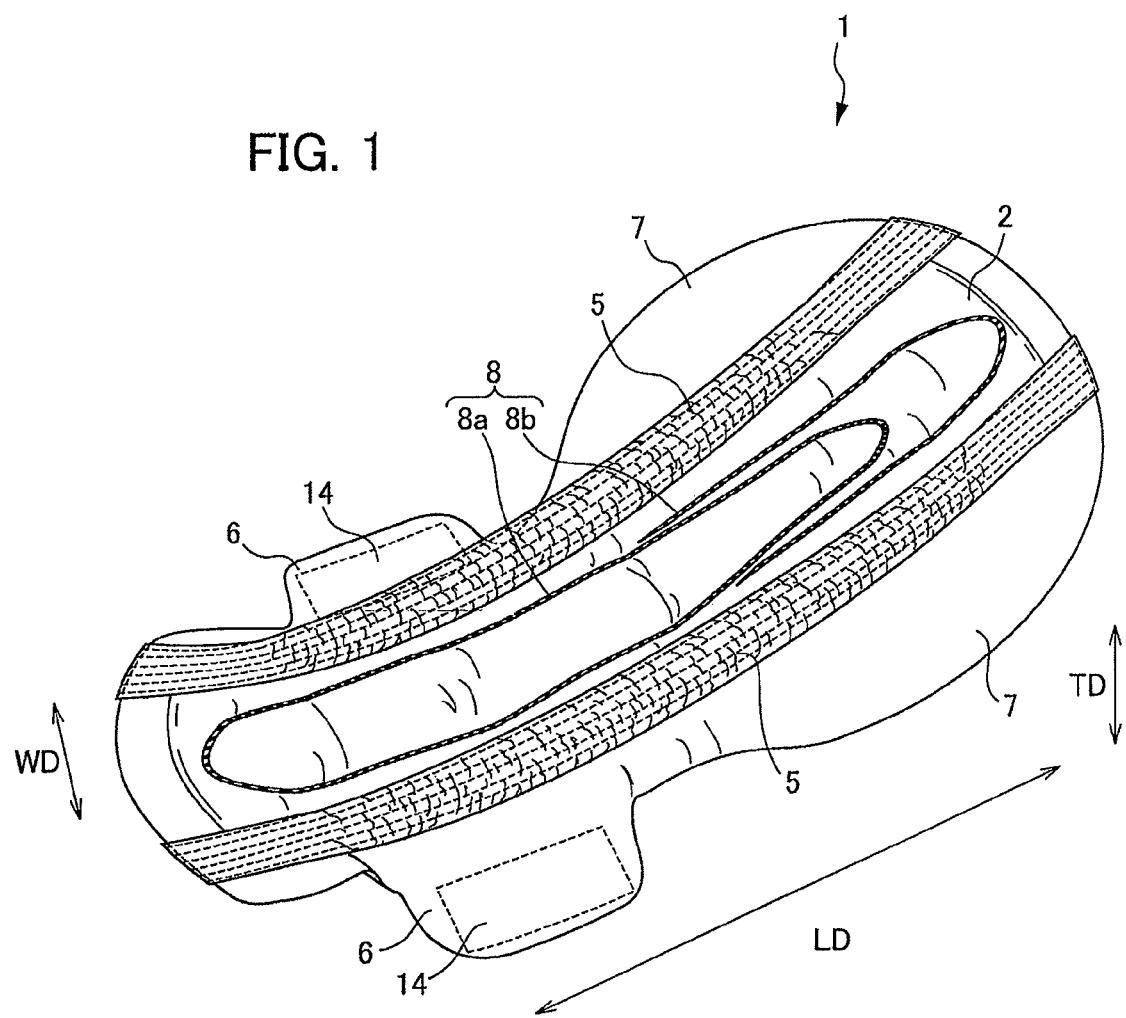
FIG. 1 is a perspective view of a sanitary napkin in a natural state as one embodiment of the absorbent article of the present invention.

EXPLANATION OF REFERENCE NUMERALS 1 sanitary napkin
2 surface sheet
3 back sheet
4 absorbent body
5 gather
6 wing
7 posterior flap
8 leak-proof groove portion
9 sheet member
10 three-dimensional-shaped portion
11 connecting portion
12 third connecting portion
13 elastic member

DETAILED DESCRIPTION OF THE INVENTION

Hereinafter, a preferred embodiment of the present invention is explained with reference to the drawings.

Figure 2:
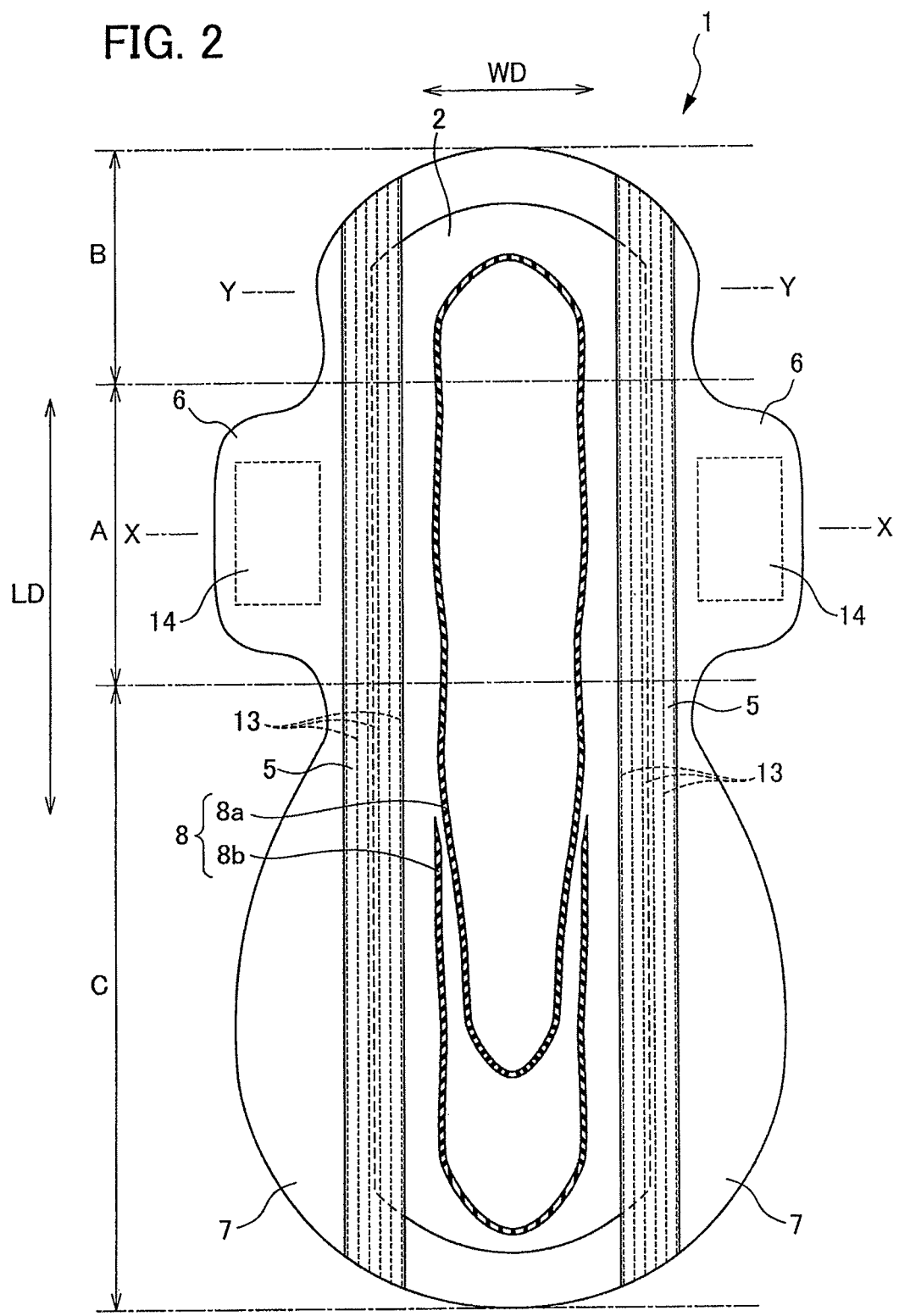
FIG. 2 is a plan view of the sanitary napkin shown in FIG. 1, when observed from the surface sheet side in a natural state.
Figure 3:
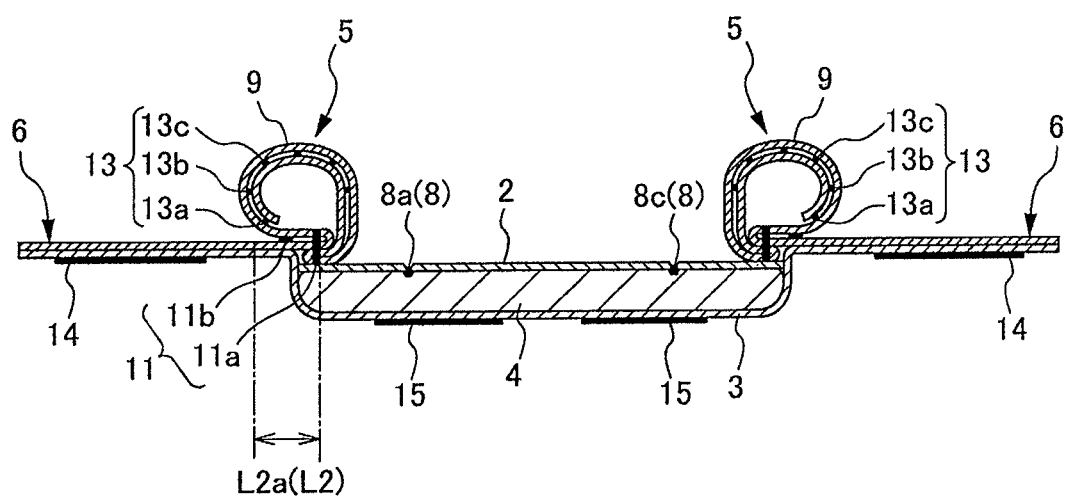
FIG. 3 shows a cross sectional view of FIG. 2 taken along the line X-X.

A sanitary napkin 1 of the present embodiment has an elongated shape as shown in FIGS. 1 to 3, and provided with a liquid-permeable surface sheet 2 as a surface layer; a liquid-impermeable back sheet 3 as a back layer; and an absorbent body 4 as a liquid-retainable absorbent layer arranged between them in an interposing way. A pair of gathers 5 and 5 are arranged in both sides of the longitudinal direction to the side of a surface sheet 2 of the sanitary napkin 1, in such a way that the pair of gathers are separated from each other, and have hollow portions formed by sheet member 9. The pair of gathers 5 and 5 stand up on the skin contacting side in the vicinity of the side edges of the absorbent body 4. Moreover, a pair of wings 6 and 6 are formed extending outward in the width direction, on both sides of the longitudinal direction of the sanitary napkin 1.

The surface layer is a layer constituting a face of the side abutting the skin of the wearer at the time of wearing the absorbent article, and, in the present embodiment, the surface layer includes the surface sheet 2 and the sheet member 9. Moreover, the surface layer includes a second sheet (not shown) arranged between the surface sheet and the absorbent body.

The back layer is a layer constituting a face of the non-skin contacting side of the absorbent article, and, in the present embodiment, the back layer includes the back sheet 3.

The absorbent layer includes the absorbent body 4 and a core-wrapping material (not shown) covering the absorbent body 4.

As shown in FIG. 2, the sanitary napkin 1 has a central portion A which is a portion opposed to the wearer's excretion part at the time of the wearing; an anterior portion B which is arranged more ventrally than the central portion A, to the wearer, at the time of the wearing; and a posterior portion C which is arranged more dorsally than the central portion A at the time of the wearing.

As shown in FIG. 2 and FIG. 3, the surface sheet 2 covers the entire area of the top surface of the absorbent body 4. The back sheet 3 covers the entire area of the under surface of the absorbent body 4. The back sheet 3 extends outward in the width direction from the side edges of the absorbent body 4 in the position of the central portion A, thereby forming part of a pair of wings 6 and 6. Moreover, the back sheet 3 extends outward in the width direction from the side edges of the absorbent body 4 in the position of the posterior portion C as well, thereby forming part of a pair of posterior flaps 7 and 7. In the central portion A and the posterior portion C, the sheet member 9, which forms a pair of gathers 5 and 5 to be described later, extends outward in the width direction, thereby forming part of the pair of wings 6 and 6 and part the pair of posterior flaps 7 and 7. That is to say, the pair of wing 6 and 6 and the pair of posterior flaps 7 and 7 include the sheet member 9 and the back sheet 3, and are formed by joining the sheet member 9 and the back sheet 3. The surface sheet 2 and the back sheet 3 extend from the front edge and the rear edge of the absorbent body 4, and are joined to each other in the extended portions.

Figure 4:
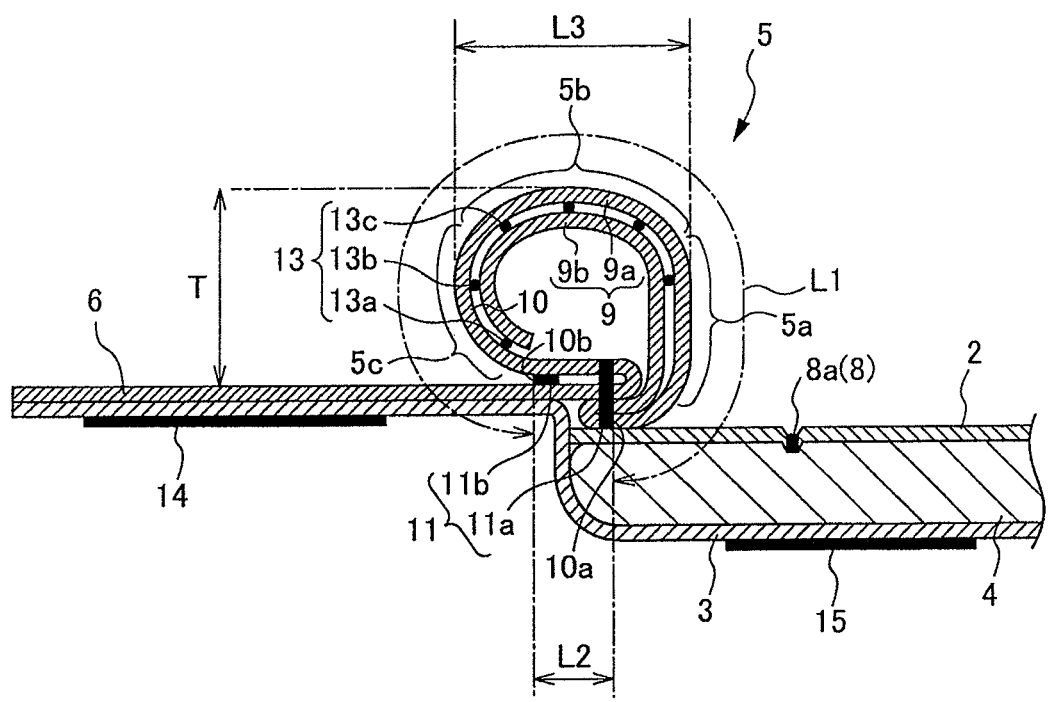
FIG. 4 is a partially enlarged view of FIG. 3.

As shown in FIG. 3 and FIG. 4, wing adhesive parts 14 and 14 are provided to the under surface side of the back sheet in the pair of wings 6 and 6 respectively. Moreover, main-body adhesive parts 15 are provided to the under surface side of the back sheet 3 in the main-body portion (the region in which the absorbent body 4 is arranged) of the sanitary napkin 1. The main-body adhesive parts 15 are provided in two lines extending in the longitudinal direction of the sanitary napkin 1.

The wing adhesive parts 14 and the main-body adhesive parts 15 are formed by applying a hot melt adhesive to the under surface side of the back sheet 3.

As shown in FIG. 3, leak-proof groove portions 8 are provided to the surface sheet side of the absorbent body 4, the absorbent body 4 and the surface sheet being compacted and consolidated into the leak-proof groove portions 8. As shown in FIG. 2, the pair of gathers 5 and 5 are located outward in the width direction of the leak-proof groove portions 8. The shape of the leak-proof groove portions 8 is substantially symmetrical about a longitudinal centerline (not shown) of the sanitary napkin 1. In the present embodiment, the leak-proof groove portions 8 include a first leak-proof groove portion 8a which is provided in a range from the anterior portion B to the posterior portion C, and a second leak-proof groove portion 8b which is provided in the posterior portion C. The first leak-proof groove portion 8a has an elongated circular shape. Moreover, as shown in FIG. 2, the first leak-proof groove portion 8a has, in the central portion A, a shape that is convexly curved outward in the width direction. The second leak-proof groove portion 8b is provided outward the first leak-proof groove portion 8a, and has a shape that is convexly curved backward. The front ends of the second leak-proof groove portion 8b are located in the vicinity of the first leak-proof groove portion 8a, but are not joined to the first leak-proof groove portion 8a.

As shown in FIG. 3 and FIG. 4, the pair of gathers 5 and 5, which are arranged in both sides of the sanitary napkin 1, are formed from the sheet member 9. As for the pair of gathers 5 and 5, the sheet member 9 has a three-dimensional-shaped portion 10 which is outwardly convex in the width direction on the skin contacting side in the sanitary napkin 1, and the three-dimensional-shaped portion 10 is joined to the surface layer and/or the back layer with a connecting portion 11 which is formed to extend in the longitudinal direction of the sanitary napkin 1. This three-dimensional-shaped portion 10 is configured such that a hollow portion is provided inside thereof, thereby forming the gather 5 having a three-dimensional shape.

As shown in FIG. 4, the connecting portion 11 includes a first connecting end 10a which forms an end inward in the width direction in the three-dimensional-shaped portion 10, and a second connecting end 10b which forms an end outward in the width direction in the three-dimensional-shaped portion. Moreover, the first connecting end 10a is located in a region in which the absorbent body 4 is arranged in the surface layer, and the second connecting end 10b is located in a region more outward in the width direction than the outer edge of the absorbent body 4 in the absorbent layer and/or the back layer, at least in regions in which the pair of wings 6 and 6 are arranged.

In the present embodiment, the second connecting end 10b is located in a region in the back sheet 3 more outward in the width direction than the side edges of the longitudinal direction of the absorbent body 4, over a substantially entire area in the longitudinal direction of the sanitary napkin 1. The case where the second connecting end 10b is located in the region in the back sheet 3 includes not only a case where the second connecting end 10b is formed by joining the sheet member 9 and the back sheet 3, but also a case where the second connecting end 10b is formed by joining the sheet member 9 arranged on a top surface of the back sheet 3, or joining another seat and the sheet member 9.

Because of the presence of the thick absorbent body 4, the rigidity is higher in regions in which the first connecting ends 10a are located in the surface layer on which the absorbent body 4 is arranged. On the other hand, since the absorbent body 4 is not arranged in the region in which the second connecting end 10b is located, the rigidity is lower in this region than that in the region in which the first connecting end 10a is located.

As shown in FIG. 3 and FIG. 4, the connecting portion 11 includes a first connecting portion 11a which is formed inward in the width direction of the sanitary napkin 1, and a second connecting portion 11b which is formed more outward in the width direction than the first connecting portion. The first connecting end 10a is formed in the first connecting portion 11a, and the second connecting end 10b is formed in the second connecting portion 11b.

The first connecting portion 11a is formed by a heat embossing process which joins the sheet member 9 and the surface sheet 2. The second connecting portion is formed in such a way that the folded parts of the sheet member 9 are joined each other with a hot-melt adhesive.

In the present embodiment, in the three-dimensional-shaped portion 10, the ratio (L1/L2) of the length L1 from the first connecting end 10a to the second connecting end 10b and the distance L2 between the connecting ends, which is the distance between the first connecting end 10a and the second connecting end 10b, is preferably not less than 2, more preferably between 2 and 15 inclusive, and further preferably between 5 and 11 inclusive.

Furthermore, as shown in FIG. 4, the cross-sectional shape of the gather 5 in the width direction is substantially Ω-shaped, in which the largest width L3 of the three-dimensional shape of the gathers 5 is greater than the distance L2 between the connecting ends.

In the present specification, the substantial Ω-shape includes, in the cross-sectional shape in the width direction of the gather having the hollow three-dimensional shape, a shape in which the largest width is greater than the length at the bottom, and also includes, for example, a shape in which the cross-sectional shape of the gather is inclined outward or inward in the width direction.

In cases where the ratio of the length L1 from the first connecting end 10a to the second connecting end 10b in the three-dimensional-shaped portion 10 in relation to the length L2 between the connecting ends (the first connecting end 10a and the second connecting end 10b) is less than 2, the gather 5 cannot form a three-dimensional shape having a sufficient hollow portion, thereby it is apprehended that it is impossible to obtain a superior effect of preventing side leakage.

Figure 6:
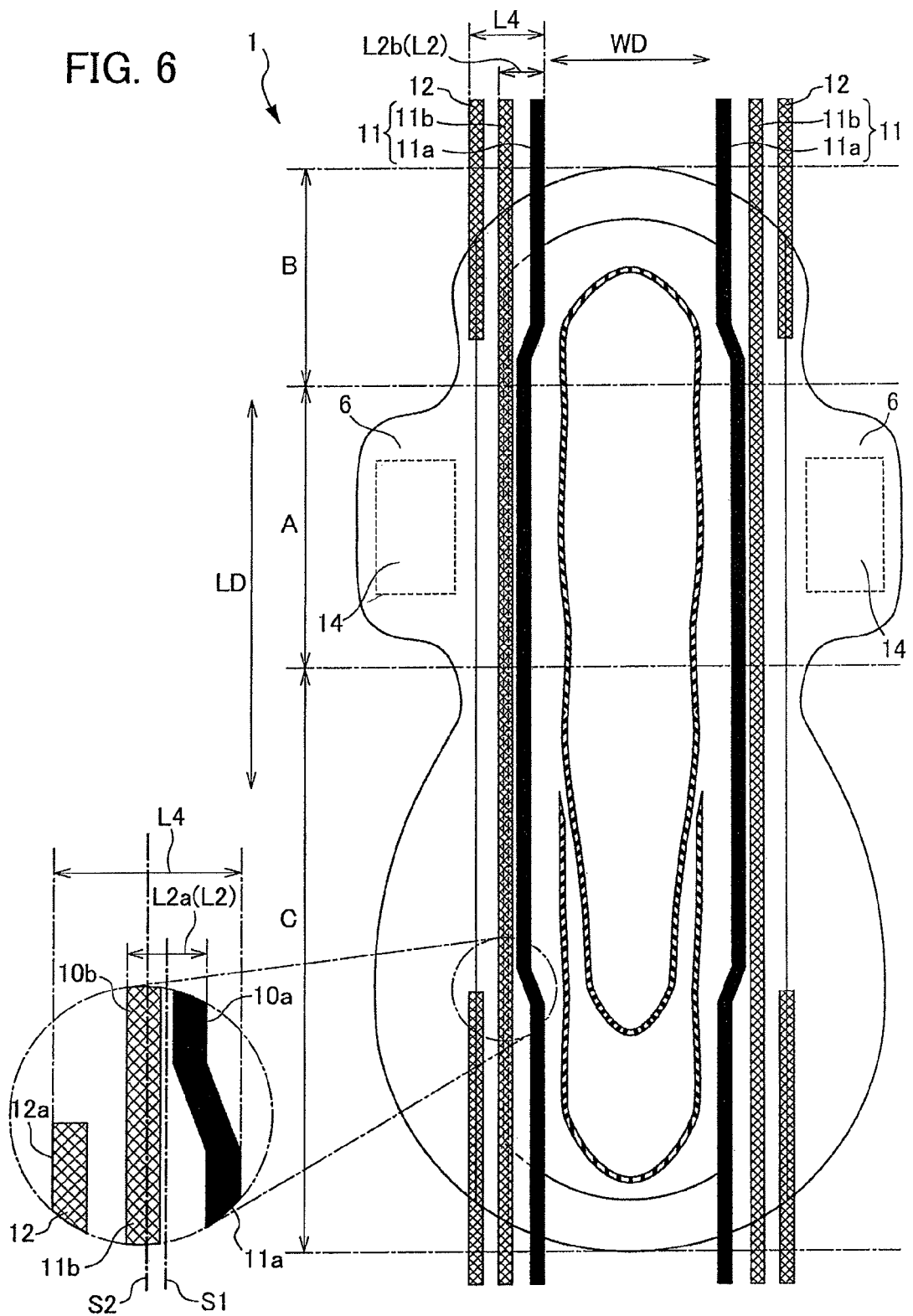
FIG. 6 is a diagram for showing an arrangement of a first connecting portion, a second connecting portion and a third connecting portion, in the absorbent article shown in FIG. 1.

The distance L2b between the connecting ends at both ends in the longitudinal direction of the sanitary napkin 1 is greater than the distance L2a between the connecting ends in the central portion A in the longitudinal direction of the sanitary napkin 1 (see FIG. 6). Specifically, from the viewpoint of increasing the standing stability of the gathers 5, it is preferable that the length L2b between the connecting ends at both ends in the longitudinal direction of the sanitary napkin 1 be 1 to 26 mm greater than the distance L2a between the connecting ends in the central portion A in the longitudinal direction of the sanitary napkin 1.

Figure 5:
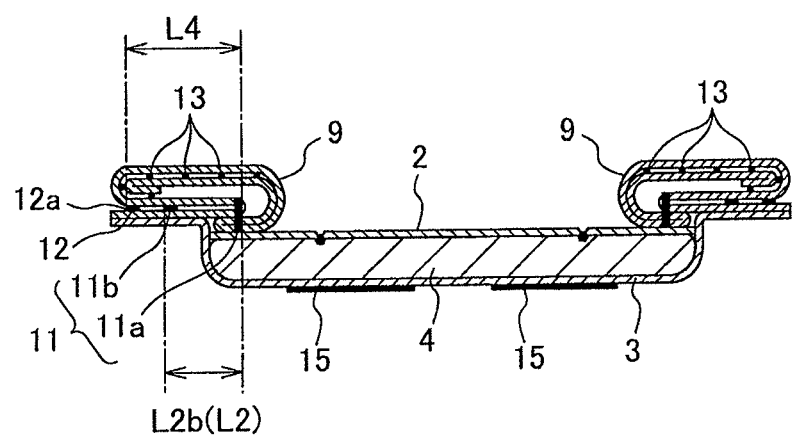
FIG. 5 is a cross-sectional view of FIG. 2 taken along the line Y-Y.

As shown in FIG. 5, third connecting portions 12, which join the sheet member 9 to the surface layer or the back layer outward the connecting portion 11, are respectively formed at both ends of the longitudinal direction the pair of gathers 5 and 5. The distance L4 between an outer end 12a in the third connecting portion 12 and the first connecting end 10a is longer than the distance L2a between the connecting ends in the longitudinal direction of the central portion A of the sanitary napkin 1 (see FIG. 6). In the present embodiment, as shown in FIG. 5, the third connecting portion 12 is formed in such a way that the sheet members 9 are joined to each other more outward in the width direction than the second connecting portion 11b by using a hot-melt adhesive.

In the present embodiment, since the pair of gathers 5 and 5 are joined to the surface layer by the third connecting portions 12 at the front edge and the rear edge of the longitudinal direction, the pair of gathers 5 and 5 do not have a three-dimensional shape without standing up in the front edge and the rear edge. That is to say, the pair of gathers 5 and 5 are planar at both ends of the longitudinal direction of the sanitary napkin 1. In a region between the front edge and the rear edge of the longitudinal direction of the sanitary napkin 1, in which the third connecting portions 12 are not provided, the pair of gathers 5 and 5 stand up on the skin contacting side, thereby forming a hollow three-dimensional shape.

The range, in which the third connecting portions 12 are formed, substantially corresponds to the region having the distance L2b between the connecting ends at both ends of the longitudinal direction of the sanitary napkin 1.

It is preferable that the range having the distance L2b between the connecting ends at both ends of the longitudinal direction of the sanitary napkin 1, i.e. the range in which the third connecting portions are formed, be the range of 40 to 70 mm from the front end in the anterior portion B of the sanitary napkin 1. Moreover, it is preferable that the range be 70 to 120 mm from the rear end in the posterior portion C.

In cases where the range, in which the third connecting portions 12 are formed, is less than 40 mm from the front end in the anterior portion B of the sanitary napkin 1, and in cases where the range is less than 70 mm from the rear end in the posterior portion C, the length of the standing portion of the gathers 5 having a three-dimensional shape becomes longer, thereby it is apprehended that the gathers 5 tend to collapse. Moreover, it is apprehended that, in the posterior portion C, the gathers 5 having a three-dimensional shape collide with the buttocks of the wearer, thereby causing uncomfortability.

In cases where the range, in which the third connecting portions 12 are formed, is more than 70 mm from the front end in the anterior portion B of the sanitary napkin 1, and in cases where the range is more than 120 mm from the rear end in the posterior portion C, the length of the standing portion of the gathers 5 having a three-dimensional shape becomes shorter, and the standability of the gathers 5 is decreased, thereby it is apprehended that the fitness while in use is decreased.

Moreover, as shown in FIG. 6, a center S1 in the width direction of the connecting portion 11 in the central portion A in the longitudinal direction of the sanitary napkin 1 is located more inward in the width direction than a center S2 between the outer end 12a in the third connecting portion 12 and the first connecting end 10a. Specifically, it is preferable that the center S1 in the width direction of the connecting portion 11 be located inward in the width direction, by approximately between 0.5 to 13 mm inclusive, in relation to the center S2 between the outer end 12a in the third connecting portion 12 and the first connecting end 10a.

A plurality of elastic members 13 are respectively arranged to the pair of gathers 5 and 5. The plurality of elastic members 13 are arranged on the surface of, or inside, the sheet member 9 with predetermined intervals along the longitudinal direction of the sanitary napkin 1. The plurality of elastic members 13 are joined, in an expanded state, to the sheet member 9 by using a hot-melt adhesive. When the plurality of elastic members 13 are joined to the sheet member 9, it is preferable that the joining to the sheet member 9 be performed by applying the hot-melt adhesive to the plurality of elastic members 13, from the viewpoint of reducing the coated area of the hot-melt adhesive and of improving the touch.

In the present embodiment, as shown in FIG. 3 to FIG. 5, six of the plurality of elastic members 13 are arranged to each of the pair of gathers 5 and 5, and the plurality of elastic members 13 are respectively arranged along the longitudinal direction with substantially equal intervals in the width direction of the sheet member 9. As shown in FIG. 4, the plurality of elastic members are arranged to all of an inner side 5a, a top side 5b and an outer side 5c in the three-dimensional shape of the pair of gathers 5 and 5.

Among the plurality of elastic members 13 which are arranged to the outer side 5c, the first elastic member 13a which is arranged in the nearest location to the second connecting end 10b is located more inward in the width direction of the sanitary napkin 1 than the second elastic member 13b which is adjacent to the first elastic member 13a Moreover, the third elastic member 13c, which is adjacent to the second elastic member 13b, is located more inward in the width direction of the sanitary napkin 1 than the second elastic member 13b. That is to say, the second elastic member 13b is located in the outermost position in the width direction, and the first elastic member 13a and the third elastic member 13c, which are adjacent to the second elastic member 13b, are located inward thereof.

The plurality of elastic members 13 are arranged in the outer side 5c in this way, as a result of which the sanitary napkin 1 of the present embodiment makes it possible to maintain the substantial Ω-shape of the gather 5 in a stable state.

Moreover, since the first elastic member 13a and the third elastic member 13c, which are adjacent to both sides of the second elastic member 13b, are located inward in the width direction of the second elastic member 13b, resistance to forces from the width direction is increased regarding the gathers 5 of the present embodiment. Accordingly, even in cases where the sanitary napkin 1 receives forces in the width direction, the gathers 5 having a three-dimensional shape are hard to collapse.

The sanitary napkin 1 of the present embodiment has a shape that is concavely curved on the skin contacting side in the longitudinal direction in a natural state, because of the contractive force of the plurality of elastic members 13 which are arranged in an expanded state in the sheet member 9. It should be noted that the natural state refers to a state where no external forces other than the gravity are acting on the sanitary napkin 1

It should also be noted that at least part of the plurality of elastic members 13 is preferably arranged to the inner side 5a or the outer side 5c which are sides of the pair of gathers 5 and 5, from the viewpoint of maintaining the three-dimensional shape of gathers 5 in a stable state.

From the viewpoint of maintaining the three-dimensional shape of the gathers 5 in a superior state, the interval of the plurality of elastic members 13 is preferably between 3 to 10 mm inclusive, and more preferably between 4 to 7 mm inclusive.

From the viewpoint of maintaining the three-dimensional shape of the gathers 5 in a stable state, the number of the plurality of elastic members, which are arranged to the sheet member 9, is preferably between 4 to 10 inclusive. In cases where the number of the elastic members 13 is not more than three, it is hard to form the substantial Ω-shape, thereby it is apprehended that it becomes hard to achieve the effect of preventing the side leakage. In cases where the number of the elastic members 13 is not less than 11, the rigidity of the gathers 5 is increased, thereby it is apprehended that the touch is deteriorated.

It is preferable that the tension, which is applied when the plurality of elastic members 13 are arranged to the sheet member 9, be gradually increased from the top side 5b to the inner side 5a and the outer side 5c in the gather 5 having a three-dimensional shape. The tension is gradually increased from the top side 5b to the inner side 5a and the outer side 5c, thereby making it possible to configure the gathers 5 which are less likely to collapse due to the forces in the width direction.

Moreover, it is preferable that the difference of the tension of the plurality of elastic members 13 to be arranged be within 300 gf/25 mm.

Each of the plurality of elastic members 13 has a chromatic color, and the chromatic color in each of the plurality of elastic members 13 is visible through the sheet member 9. In the present embodiment, each of the plurality of elastic members 13 uses blue as the chromatic color. The color of the plurality of elastic members 13 is not particularly limited as long as it is not white, but it is preferably a color which achieves visibility as well as a feeling of cleanliness. From the viewpoint that the chromatic color of the elastic members 13 should be easily visible through the sheet member 9, the color of the sheet member 9 is preferably transparent, semitransparent, white, etc. which are likely to transmit the chromatic color.

In this way, since the plurality of elastic members 13 having a chromatic color are visible through the sheet member 9 in the gathers 5 having a three-dimensional shape, even such a gather, in which free ends are not formed, as in the present embodiment gives the wearer a three-dimensional impression of a convex three-dimensional structure at the skin contacting side. This provides the feeling of security (security against the side leakage) regarding the sides of the sanitary napkin 1, as a result of which the wearer is provided with the feeling of security regarding the sanitary napkin 1 itself.

As shown in FIG. 4, each of the pair of gathers 5 and 5 has a two-layered portion which is formed by folding back the sheet member 9. The plurality of elastic members 13 are arranged in such a way to be interposed between an outer layer 9a and in inner layer 9b in the two-layered portion.

In the present embodiment, the two-layered portion is formed in an entire area of the inner side 5a, an entire area of the top side 5b, and an upper area of the outer side 5c in the gather 5. All of the six elastic members 13 are arranged in such a way to be interposed between the outer layer 9a and the inner layer 9b in the two-layered portion. The outer layer 9a and the inner layer 9b are joined by means of a hot-melt adhesive applied to the plurality of elastic members 13.

It is preferable that the gathers 5, which include the sheet member 9 and the plurality of elastic members 13, have appropriate rigidity from the viewpoint of maintaining the hollow three-dimensional shape in a stable state and of obtaining a superior feeling of wearing. However, if the rigidity is too high, the feeling while in use may be deteriorated.

Moreover, as for the physical properties of the expansion and contraction of the gathers 5, a stress at the time when the gather 5 is extended 5 to 50% in the longitudinal direction of the sanitary napkin 1 is preferably 50 to 500 gf/25 mm width, and more preferably 100 to 300 gf/25 mm width. In cases where the stress is less than 50 gf/25 mm width, the expansion and contraction force of the gathers 5 is weak, thereby it is apprehended that the standability of the gathers 5 is deteriorated. In cases where the stress is more than 500 gf/25 mm width, the degree of the curve in the longitudinal direction of the sanitary napkin 1 is high, thereby it is apprehended that the fitness with the wearer's body is decreased.

The preferable range of numerical values in each configuration of the sanitary napkin of the present embodiment is described below.

The length L1 of the sheet member 9 from the first connecting end 10a to the second connecting end 10b in the three-dimensional-shaped portion 10 is preferably 30 to 58 mm, and more preferably 16 to 58 mm, from the viewpoint of securing the standing height of the gathers 5. The standing height of the gathers 5 is preferably 15 to 25 mm, and more preferably 10 to 30 mm. In cases where the standing height T of the gathers 5 is less than 10 mm, it is apprehended that the effect of preventing the side leakage is decreased, and that the wearer is not provided with the feeling of security that enough function of preventing the side leakage is given. In cases where the standing height T of the gathers 5 is higher than 30 mm, it is apprehended that the fitness to the wearer's body by the gathers 5 is excessively strong, and that the fitness between the absorbent body 4 and the wearer's body is decreased.

From the viewpoint of forming the gathers 5 with superior standability, the distance L2 between the connecting ends, which is the distance between the first connecting end 10a and the second connecting end 10b, is preferably 5 to 20 mm, and more preferably 5 to 15 mm. In cases where the distance L2 between the connecting ends is less than 3 mm, it is apprehended that the gathers 5 are likely to collapse due to the forces applied from the width direction of the sanitary napkin 1. In cases where the gathers 5 collapse in this way, it is apprehended that the collapsed gathers 5 cover the absorption face of the absorbent body 4. In cases where the distance L2 between the connecting ends exceeds 20 mm, the hollow portion is hard to be formed in the gather 5, and a gap is likely to be caused between the gathers 5 and the wearer's body, thereby it is apprehended that the leak-proof effect is decreased. From the viewpoint of preventing the gathers 5 from easily deforming due to the forces applied from the width direction of the sanitary napkin 1, the maximum width L3 in the three-dimensional shape of the gathers 5 needs to be greater than the distance L2 between the connecting ends, which is the distance between the first connecting end 10a and the second connecting end 10b, and is specifically preferably 5 to 38 mm, and more preferably 6 to 30 mm.

The distance L4 between the outer end 12a in the third connecting portion 12 and the first connecting end 10a is preferably 25 to 35 mm. In cases where the distance L4 between the outer end 12a in the third connecting portion 12 and the first connecting end 10a is more than 35 mm, the contact area of the skin of the wearer and the sheet member 9 constituting the gathers 5 becomes wide, thereby it is apprehended that a feeling of wearing is deteriorated.

Construction materials of the sanitary napkin 1 of the present embodiment are described.

As the surface sheet 2, it is possible to use nonwoven fabrics with or without pores or porous plastic sheets. As the back sheet 3, it is possible to use a hydrophobic nonwoven fabric, an impermeable plastic film, or a laminated sheet of the nonwoven fabric and the impermeable plastic film. Alternatively, as the back sheet 3, it is also possible to use a SMS nonwoven fabric sandwiched by melt-blown nonwoven fabrics having high water-resisting property and high-strength spun-bonded nonwoven fabrics.

As the absorbent body 4, it is possible to use a fluff pulp or an airlaid nonwoven fabric as well as a high-absorbance polymer.

Examples of the fluff pulp to be used as the absorbent body 4 include chemical pulps, cellulose fibers, and artificial cellulose fibers such as rayon and acetate. Examples of the airlaid nonwoven fabric include one prepared by thermal fusion of a pulp with a synthetic fiber or fixing them by a binder. Examples of the high-absorbance polymer include starch-, acrylic acid-, and amino acid-based granular or fibrous polymers.

As the sheet member 9, water-repellent or hydrophobic materials are preferably used. Specifically, it is possible to use various non-woven fabrics such as spun lace non-woven fabrics, spun bond nonwoven fabrics, thermal bond non-woven fabric, meltblown non-woven fabrics, needle-punched nonwoven, and air through non-woven fabrics. As raw material fibers which constitute the nonwoven fabrics, it is possible to use olefin (such as polyethylene or polypropylene)-, polyester-, and polyamide-based synthetic fibers, as well as regenerated fibers such as rayon and cupra, and natural fibers such as cotton.

As the elastic members 13, it is acceptable as long as it is a stretching and contracting material, and it is possible to use filar rubber or flat rubber constituted of natural rubber, and thermoplastic elastomer such as urethane, ethylene-vinyl acetate copolymer (EVA) and PE. More specifically, examples of the thermoplastic elastomer include ones in which any of the following materials is shaped into a filar or film shape and slit into a narrow width: polybutadiene, polyisoprene, styrene-butadiene copolymer, styrene-isoprene copolymer, polyurethane, ethylene-acetic acid vinyl copolymer, and ethylene-alpha olefin copolymer.

The sanitary napkin 1 of the present embodiment having the configuration as described above is fixed to the underwear in such a way that the elongated main-body portion is arranged at the inner face of the crotch area of the underwear such as undergarment, and the pair of wings 6 and 6 are folded back to the outer side of the crotch area. The sanitary napkin 1 is fixed to the underwear in such a way that the main-body adhesive parts 15 arranged on the under surface of the main-body portion are fastened to the inner face of the crotch area, and the wing adhesive parts 14 and 14 arranged on the under surface of the pair of wing 6 and 6 are fastened to the outer surface of the crotch area.

According to the sanitary napkin 1 of the present embodiment, the first connecting end 10a in the three-dimensional-shaped portion 10 forming the gather 5 is located in a high-rigidity region which is the region in which the absorbent body 4 is arranged in the surface layer, and the second connecting end 10b, at least in regions in which the pair of wing 6 and 6 are arranged, is located in a low-rigidity region which is the region which is more outward in the width direction than the outer edge of the absorbent body 4 in the surface layer and/or the back layer. In this way, the first connecting end 10a is located in a high-rigidity region, and the second connecting end 10b is located in a low-rigidity region, thereby improving the standing stability of the three-dimensional-shaped gathers 5 having the hollow portion, in the sanitary napkin 1 of the present embodiment.

At the time of wearing the sanitary napkin 1, various forces are applied to the sanitary napkin 1. Particularly in cases where the wings are folded back to be fastened to the outer side of the crotch area such as undergarment, the wings are pulled outward to the width length. As a result, strong forces are applied in the width length to the sanitary napkin 1 as well. According to the sanitary napkin 1 of the present embodiment, in cases where the strong forces are applied outward in the width direction, the inner side 5a, which is located on the side of the first connecting end 10a in the gather, 5 is less likely to be affected by the forces in the width direction, because the first connecting end 10a is located in the high-rigidity region.

On the other hand, the outer side 5c, which is located on the side of the second connecting end 10b side, absorbs the applied forces by easily changing the shape due to the forces applied in the width direction, because the second connecting end 10b is located in the low rigidity-region.

In this way, the outer side 5c of the gather 5 is easy to deform, and the inner side 5a is less likely to be affected by the forces applied to the sanitary napkin 1. As a result, even in cases where strong forces are applied outward in the width direction, the gathers 5 respectively having the hollow portions are less likely as a whole to collapse outward in the width direction, thereby improving the standing stability of the gathers 5, and also improving the effect of preventing the side leakage.

Moreover, in cases where forces are applied inward in the width direction to the sanitary napkin 1, the gathers 5 as a whole are less likely to collapse inward in the width direction, by the action as described above.

In contrast, it has been often the case with the conventional gathers to collapse outward by forces to pull outward in the width direction. There have been cases where the article is worn to the wearer's body in a state where the gathers have collapsed, thereby resulting in the side leakage.

Particularly regarding the sanitary napkin 1 including the wings 6 and the three-dimensional-shaped gathers 5, in cases where the gathers 5 and the wings 6 are formed with a single sheet member 9, the tension to pull the wings outward in the width direction at the time of folding back the wings 6 is likely to be transmitted to the gathers 5 which are integrally formed with the wings 6, thereby making the gathers 5 more likely to collapse outward in the width direction. However, according to the sanitary napkin 1 of the present embodiment, the three-dimensional-shaped gathers 5, which respectively have the hollow portions even in cases of forming the gathers 5 and the wings 6 with a single sheet member 9, are less likely to collapse, and have a superior standing stability.

Furthermore, since the inside of the three-dimensional shape of the gathers 5 is hollow, it is possible for the gathers 5 to fit, in a planar form, with the wearer's body, and it is also possible for the three-dimensional shape of the gathers 5 to flexibly follow the physical motion of the wearer, thereby making it possible to effectively prevent leakage from width direction of the sanitary napkin 1. Furthermore, in cases where the forces are applied to the sanitary napkin 1 from the width direction, the gathers 5 of the three-dimensional shape having the hollow portion absorb and buffer the applied forces, thereby making it possible to reduce the forces applied to the absorbent body 4. As a result, the absorbent body 4 is hard to deform, and the fitness of the sanitary napkin 1 to the wearer's body is improved.

Furthermore, the connecting portion 11 includes a first connecting portion 11a which is formed inward in the width direction of the sanitary napkin 1, and a second connecting portion 11b which is formed more outward in the width direction than the first connecting portion, in which the first connecting end 10a is formed in the first connecting portion 11a, and in which the second connecting end 10b is formed in the second connecting portion 11b. In this way, the first connecting end 10a and the second connecting end 10b are formed at connecting portions which are different (separated) from each other, thereby the inner sides 5a of the gathers 5 are less likely to receive influence of the forces applied in the width direction, and the gathers 5 are less likely to collapse, as a result of which the effect of preventing the side leakage is also improved.

Moreover, in the three-dimensional-shaped portion 10 forming the gather 5, the ratio of the length L1 from the first connecting end 10a to the second connecting end 10b and the distance L2 between the connecting ends, which is the distance between the first connecting end 10a and the second connecting end 10b, is not less than 2, as a result of which the three-dimensional shape of the pair of gathers 5 and 5 is stably formed, and the gathers 5 are less likely to collapse even in cases where forces are applied to the sanitary napkin 1 from the width direction.

Moreover, the cross-sectional shape of the gathers 5 in the width direction is substantially Ω-shaped, in which the largest width L3 of the three-dimensional shape of the gathers 5 is greater than the distance L2 between the connecting ends, as a result of which the standability of the gathers 5 is improved.

Moreover, the distance L2b between the connecting ends in the vicinities of both ends in the longitudinal direction of the sanitary napkin 1 is greater than the distance L2a between the connecting ends in the central portion in the longitudinal direction of the sanitary napkin 1, as a result of which the tension to the gathers 5 in the width direction is gradually increased from the central portion to the both ends. This improves the standing stability of the three-dimensional-shaped gathers 5 in the central portion in the longitudinal direction, and makes the gathers 5 to be less likely to collapse. Furthermore, the pair of the wings 6 and 6 are arranged in the central portion in the longitudinal direction, of which the standing stability is high, therefore even in cases where forces are applied outward in the width direction to the pair of wings 6 and 6 at the time of wearing the sanitary napkin 1, the gathers 5 are less likely to collapse outward.

Furthermore, the third connecting portions 12, which join the sheet member to the surface layer or the back layer more outward in the width direction than the connecting portion, are respectively formed at both ends of the longitudinal direction the pair of gathers 5 and 5. The distance L4 between the outer end in the third connecting portion 12 and the first connecting end 10a is longer than the distance L2a between the connecting ends in the longitudinal direction of the central portion of the sanitary napkin 1. Accordingly the tension to the gathers 5 in the width direction is further increased from the central portion to the both ends. This improves the standing stability of the gathers 5 of the three-dimensional shape, and makes the gathers 5 to be less likely to collapse.

Moreover, the center in the width direction of the connecting portion 11 is located more inward in the width direction than the center between the outer end in the third connecting portion 12 and the first connecting end 10a, as a result of which the three-dimensional shape of the gathers 5 has the substantial Ω-shape that is declined outward in the width direction from the lower end to the upper end. That is to say, the pair of gathers 5 and 5 are arranged in such a way that the distance between the top ends is greater than the distance between the bottom ends. The pair of gathers 5 and 5 are arranged in such a way that the distance between the top ends is greater than the distance between the bottom ends, thereby improving the effect of preventing the side leakage of the sanitary napkin 1.

Moreover, each of the pair of gathers 5 and 5 have the plurality of elastic members 13, and the plurality of elastic members 13 are arranged on the surface of, or inside, the sheet member 9, and are arranged along the longitudinal direction, thereby making it possible to stably maintain the three-dimensional shape having the hollow portion of gather 5.

Moreover, all or part of the plurality of elastic members 13 is arranged to the respective sides of the pair of gathers 5 and 5, thereby making it possible to more stably maintain the three-dimensional shape having the hollow portion of gather 5.

Furthermore, each of the pair of gathers 5 and 5 has the two-layered portion which is formed by folding back the sheet member 9, and the plurality of elastic members 13 are arranged in such a way to be interposed between the layers of the two-layered portion, as a result of which the gathers 5, in which the plurality of elastic members 13 are arranged, have appropriate rigidity, thereby improving the standing stability of the gathers 5.

In addition, the leak-proof groove portion 8 has a shape which is convexly curved outward in the width direction in the central portion A. Accordingly, in cases where the sanitary napkin 1 receives forces from the width direction, the standing stability of the gathers 5 is improved in the central portion A which is a region corresponding to the excretion part, thereby improving the effect of preventing the side leakage. Furthermore, the absorbent body 4 is more likely to be lifted up on the skin contacting side of the wearer as a result of the forces applied from the width direction, thereby creating an effect of improving the contact between the absorbent body 4 and the excretion part of the wearer.

The present invention is not limited to the above described embodiments, but various alterations are possible within a scope of the present invention.

For example, in the present embodiment, the second connecting ends 10b are formed in the region on the back sheet 3 more outward in the width direction than the side edges in the longitudinal direction of the absorbent body 4, over a substantially entire area in the longitudinal direction of the sanitary napkin 1. However, it suffices as long as the second connecting ends 10b are formed more outward in the width direction than the side edges in the longitudinal direction of the absorbent body 4, in the central portion A which faces at least the excretion part, i.e. regions in which the wings 6 are arranged.

Moreover, in the present embodiment, as for the pair of gathers 5 and 5, the plurality of elastic members are arranged to the sheet member 9, but instead of using the plurality of elastic members, seats having contraction and expansion properties may be used as the sheet member 9. Moreover, the pair of gathers 5 and 5 may be formed with a sheet member which does not have contraction and expansion properties.

Furthermore, in the present embodiment, the gathers 5 and the wings 6 are formed with one piece of the sheet member 9, but the wings 6 may be configured with seats which are different from the seat members constituting the gathers 5.

The absorbent article of the present invention may be, in addition to sanitary napkins, urine-absorbing pads, panty liners, disposable diaper and the like.

The invention claimed is:

1. An elongated absorbent article, comprising
a surface layer having an at least partly liquid-permeable surface sheet;
a back layer having a liquid-impermeable back sheet;
an absorbent layer having a liquid-retainable absorbent body arranged between the surface and back layers; and
a pair of gathers which are formed to be separated from each other on both sides of a longitudinal direction of the surface layer, and each of which has a three-dimensional-shaped portion substantially Ω-shaped in a cross-section cut along a width direction of the gather and is configured to have a hollow portion by a sheet member, each of the pair of gathers located across an anterior portion, a posterior portion, and a central portion between the anterior portion and the posterior portion in the longitudinal direction of the absorbent article, the three-dimensional-shaped portion being joined to the surface layer and/or the back layer by a connecting portion which is formed to extend in the longitudinal direction of the absorbent article,
wherein each of the pair of gathers has a two-layer portion which defines the hollow portion, and is formed in such a way that the sheet member extends from a region more outward in the width direction than an outer edge of the absorbent body to an upper surface of an end of the absorbent body, is folded back outwardly at a first folding back portion, extends alone an outer side a top side and an inner side of the three-dimensional-shaped portion, is folded back inwardly at a second folding back portion, and extends along an inner periphery of the hollow portion within the three-dimensional-shaped portion,
wherein the connecting portion comprises a first connecting end extending in the longitudinal direction of the absorbent article, which forms an end inward in a width direction of the three-dimensional-shaped portion, and a second connecting end extending in the longitudinal direction of the absorbent article, which forms an end outward in the width direction of the three-dimensional-shaped portion, wherein the first connecting end comprises the first and second folding back portions that are overlapped and joined to each other, and the second connecting end comprises a region in which opposed surfaces of the sheet member adjacent to the first folding back portion are joined to each other.

2. The absorbent article according to claim 1, further comprising a pair of wings which are formed by extending the surface layer and/or the back layer outward in a width direction of the absorbent layer, and wherein the pair of wings are arranged in the central portion in the longitudinal direction.

3. The absorbent article according to claim 2, wherein at least a face on the surface-layer side of the pair of wings is formed with the sheet member.

4. The absorbent article according to claim 1, wherein each of the pair of gathers has a plurality of elastic members, and wherein the plurality of elastic members are arranged in such a way to be interposed between an outer layer and an inner layer in the two-layer portion.

5. The absorbent article according to claim 1, further comprising additional connecting portions formed at both longitudinal ends of the pair of gathers, the additional connecting portions are formed such that the sheet members are joined to each other more outwardly in the width direction than the second connecting end.

6. The absorbent article according to claim 5, wherein the additional connection portions pull down respective three-dimensional-shaped portions to the back layer so that a width of the three-dimensional-shaped portions is larger than a height of the three-dimensional-shaped portions.

7. The absorbent article according to claim 1, wherein the largest width of the three-dimensional-shaped portion is greater than the distance between the first and the second connecting ends.

8. The absorbent article according to claim 1, wherein the first connecting end is located in a region in which the absorbent body is arranged beneath the surface layer, the second connecting end is located in a region in which absorbent body is not arranged beneath the surface layer, a rigidity at the second connecting end is lower than a rigidity at a first connecting end, and the second connecting end is located in a region more outward in the width direction than an outer edge of the absorbent body.

9. The absorbent article according to claim 1, wherein a distance between the first and the second connecting ends in the anterior and the posterior portion is greater than a distance between the first and the second connecting ends in the central portion.

* * * * *